US005618284A

United States Patent [19]
Sand

[11] Patent Number: 5,618,284
[45] Date of Patent: Apr. 8, 1997

[54] COLLAGEN TREATMENT APPARATUS

[75] Inventor: Bruce J. Sand, Hidden Hills, Calif.

[73] Assignee: Sunrise Technologies, Fremont, Calif.

[21] Appl. No.: 484,669

[22] Filed: Jun. 7, 1995

Related U.S. Application Data

[63] Continuation of Ser. No. 227,781, Apr. 14, 1994, Pat. No. 5,484,432, which is a continuation-in-part of Ser. No. 926,331, Aug. 6, 1992, Pat. No. 5,374,265, and a continuation-in-part of Ser. No. 930,973, Aug. 17, 1992, Pat. No. 5,304,169, which is a continuation-in-part of Ser. No. 771,547, Oct. 4, 1991, abandoned, which is a continuation-in-part of Ser. No. 546,252, Jun. 29, 1990, Pat. No. 5,137,530, which is a continuation-in-part of Ser. No. 374,958, Jun. 30, 1989, Pat. No. 4,976,709, which is a continuation-in-part of Ser. No. 285,379, Dec. 15, 1988, abandoned, which is a continuation of Ser. No. 170,070, Mar. 14, 1988, abandoned, and a continuation of Ser. No. 67,381, Jun. 23, 1987, and a continuation of Ser. No. 914,169, Oct. 1, 1986, abandoned, which is a continuation-in-part of Ser. No. 781,225, Sep. 27, 1985, abandoned, said Ser. No. 926,331, is a continuation-in-part of Ser. No. 546,252, Jun. 29, 1990, Pat. No. 5,137,530.

[51] Int. Cl.$^6$ .................................................. A61N 5/06
[52] U.S. Cl. ................................................................ 606/5
[58] Field of Search .............................. 606/3–5, 13–16; 372/41

[56] References Cited

U.S. PATENT DOCUMENTS

| | | |
|---|---|---|
| 3,776,230 | 12/1973 | Neefe . |
| 4,326,529 | 4/1982 | Doss et al. . |
| 4,330,763 | 5/1982 | Esterowitz . |
| 4,381,007 | 4/1983 | Doss . |
| 4,391,275 | 7/1983 | Fankhauser et al. . |
| 4,404,033 | 9/1983 | Steffan .................................... 106/161 |
| 4,444,787 | 4/1984 | Moorhead .............................. 424/304 |
| 4,461,294 | 7/1984 | Baron . |
| 4,537,193 | 8/1985 | Sand . |
| 4,538,608 | 9/1985 | L'Esperance . |
| 4,558,698 | 12/1985 | O'Dell . |
| 4,580,559 | 4/1986 | L'Esperance . |
| 4,665,913 | 5/1987 | L'Esperance . |
| 4,669,466 | 6/1987 | L'Esperance . |
| 4,799,478 | 1/1989 | Fedorov et al. . |
| 4,881,543 | 11/1989 | Trembly et al. . |

(List continued on next page.)

FOREIGN PATENT DOCUMENTS

| | | |
|---|---|---|
| 402250 | 12/1990 | European Pat. Off. . |
| 0484005A | 10/1991 | European Pat. Off. . |
| 0484005A1 | 6/1992 | European Pat. Off. . |
| 3148748 | 7/1983 | Germany . |
| 929097 | 1/1982 | U.S.S.R. . |
| WO8603938 | 7/1986 | WIPO . |
| WO9012618 | 4/1990 | WIPO . |
| WO9201430 | 2/1992 | WIPO . |
| WO9407424 | 4/1994 | WIPO . |
| WO9410345 | 5/1994 | WIPO . |

OTHER PUBLICATIONS

Horn et al., "New Refractive Method for Laser Thermal Keratoplasty With the Co:MgF$_2$ Laser," *Journal of Cataract and Refractive Surgery*, vol. 16, pp. 611–616. (Sep. 1990).

Spears et al., "Corneal Refractive Correction by Laser Thermal Keratoplasty", *SPIE Laser–Tissue Interaction*, vol. 1202, pp. 334–340 (1990).

(List continued on next page.)

*Primary Examiner*—Max Hindenburg
*Attorney, Agent, or Firm*—Majestic, Parsons, Siebert & Hsue

[57] ABSTRACT

A method and apparatus for controlled thermal shrinkage of collagen tissue by irradiation with coherent energy in the wavelength band of 1.80 to 2.55 microns as generated by a laser. A specific application to ophthalmological corneal reshaping is described. A method for shrinkage of collagen tissue by application of coherent infrared energy, in which the threshold shrinkage temperature is substantially reduced by application of a reagent such as lysozyme to the tissue prior to heating. The method is especially useful in ophthalmology for shape modification of a cornea, and is enhanced by using a corneal collagen shield as a carrier and delivery agent for the reagent and an admixed anaesthetic.

23 Claims, 5 Drawing Sheets

U.S. PATENT DOCUMENTS

| | | |
|---|---|---|
| 4,884,884 | 12/1989 | Reis . |
| 4,887,592 | 12/1989 | Loertscher . |
| 4,907,585 | 3/1990 | Schachar . |
| 4,907,586 | 3/1990 | Bille et al. . |
| 4,907,587 | 3/1990 | Fedorov et al. . |
| 4,931,053 | 6/1990 | L'Esperance . |
| 4,976,709 | 12/1990 | Sand . |
| 5,112,328 | 5/1992 | Taboada et al. . |
| 5,152,759 | 10/1992 | Parel et al. . |
| 5,230,334 | 7/1993 | Klopotek . |
| 5,263,951 | 11/1993 | Spears . |
| 5,281,211 | 1/1994 | Parel et al. . |
| 5,334,190 | 8/1994 | Seiler . |
| 5,348,551 | 9/1994 | Spears et al. . |
| 5,409,479 | 4/1995 | Dew et al. . |
| 5,437,658 | 8/1995 | Muller et al. . |

OTHER PUBLICATIONS

Chandonet et al., "Corneal Reshaping by Laser–Induced Thermokeratoplasty," *Lasers and Electro–Optics Society Annual Meeting Conference Proceedings*, pp. 192, 457–458 (1989).

Wright, "Laser Thermokeratoplasty Shows Promise," *Opthalmology*, pp. 1 and 30, (Jun. 1, 1989).

Householder, "Laser Induced Thermal Kerotoplasty", *SPIE Laser Surgery: Advanced Characterization, Therapeutics and Systems*, vol. 1066, pp. 18–23 (1989).

Horn, "A Method For Refractive Correction Using Laser Thermokeratoplasty", orally presented at the *2nd American–Intl. Congress on Cataract, IOL and Refractive Surgery*, in Washington, D.C. (Apr. 25, 1989).

Seiler et al., "Laser Thermokeratoplasty by Means of a Pulsed Holmium: YAG Laser for Hyperopic Correction", *Refractive & Corneal Surgery*, vol. 6, pp. 335–339, Sep. 10, 1990.

Cartlidge et al., "A Laser Surgical Unit for Photoablative and Photothermal Keratoplasty," *Ophthalmic Technologies*, 1423 (1991), pp. 167–174.

Rol et al., "Computed Estimation of Visual Acuity after Laser Refractive Keratectomy," *Ophthalmic Technologies*, 1423 (1991), pp. 89–93.

Seiler et al., "Laserkoagulation der Hornhaut mit eimen Holmiun:YAG–Laser zur Hyperopiekorrektur," *Fortschr Ophthalmol*, 88 (1991), pp. 121–124.

Koch et al., abstract of "HF Chemical Laser Photothermal Keratoplasty," *ARVO*, 32:4 (Annual Meeting abstract Issue) (1991), p. 994.

Berry et al., abstract of "Temperature Distributions in Laser––Irradiated Corneas," *ARVO*, 32:4 (Annual Meeting Abstract Issue) (1991), p. 994.

Parel et al., abstract of "Laser Photo Thermal Keratoplasty," *ARVO*, 32:4 (Annual Meeting Abstract Issue) (1991), p. 995.

Chandonnet et al., "$CO_2$ Laser Annular Thermokeratoplasty: A Preliminary Study," *Lasers in Surgery and Medicine*, 12 (1992), pp. 264–273.

Thompson et al., "Therapeutic and Diagnostic Application of Lasers in Ophthalmology," *Proceedings of the IEEE*, 80:6 (1992), pp. 838–860.

Durriet et al., "Application of the Holmium:YAG Laser for Refractive Surgery," reprint of paper to be published in *SPIE Proceedings*, 1644 (1992), 5 pages.

Seiler, "Ho:YAG Laser Thermokeratoplasty foir Hyperopia," *Contemporary Refractive Surgery*, 5:4 (1992), pp. 773–780.

Cotliar et al., "Excimer Laser Radial Kerototomy," *Ophthalmology*, vol. 92 No. 2, Feb. 1985, pp. 206–207.

Mainster, "Ophtalmic Applications of Infrared Lasers–Thermal Considerations," *Invt. Opth. Visual Sci*, Apr. 1979.

Doss et al., "An Electrochemical Technique for the Acceleration of Corneal Curvature," *Los Alamos Sci Lab.*, Feb. 1978.

Chetvertukhin et al., "Refractive Thermo– and Laser Keratoplasty", *Vestn. Oftal.*, pp. 67–69 (USSR 1982), and English Translation.

Bargeron et al., "Calculated and Measured Endothelial Temperature Histories of Excised Rabbit Corneas Exposed to Infrared Radiation", *Experimental Eye Research*, vol. 32, No. 2, pp. 241–250 (1981).

Stuck et al., "Ocular Effects of Holmium (2.06 μm) and Erbium (1.54 μm) Laser Radiation", *Health Physics*, vol. 40, pp. 835–846 (1981).

Stringer et al., "Shrinkage Temperature of Eye Collagen", *Nature*, vol. 204, No. 4965, p. 1307 (1964).

Jackson, D.S. "The Nature of Collagen–Chrondroitin Sulphate Linkages in Tendon", *Rheumatism Research Center, University of Manchester*, vol. 56, pp. 699–703, Oct. 12, 1953).

Jackson, D.S. "Chrondroitin Sulphuric Acid as a Factor in the Stability of Tendon", *Rheumatism Research Center, University of Manchester*, vol. 54, pp. 638–641, Jan. 9, 1953).

Rowsey et al., "Los Alamos Keratoplasty Techniques", *Contact & Intraocular Lens Medical Jnl*, Mar. 1980.

Gassett et al., "Thermokeratoplasty for the Treatment of Keratocornus", *Amer. Jnl. of Ophthalmology*, Feb. 1975.

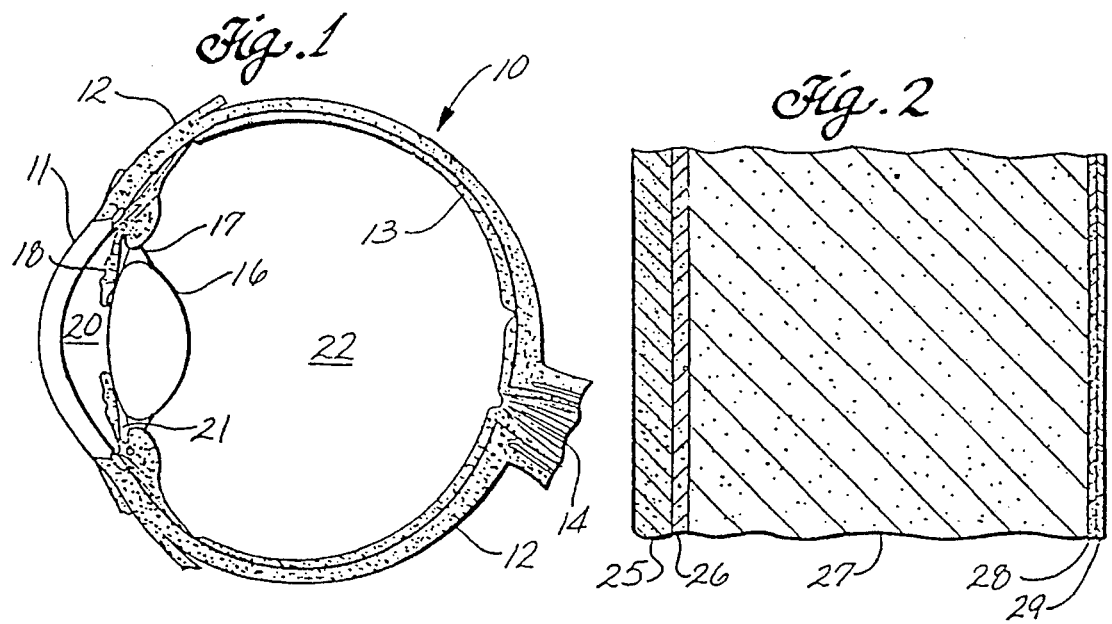
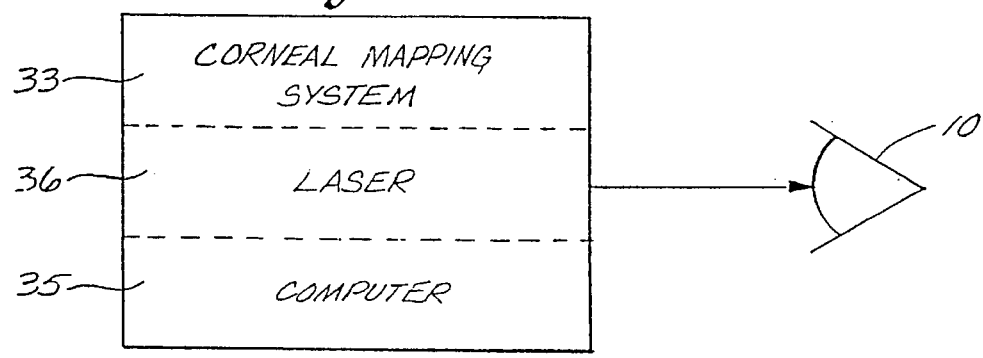
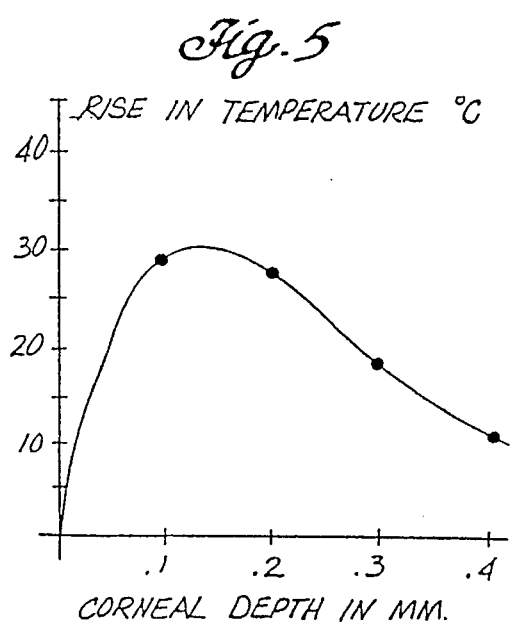

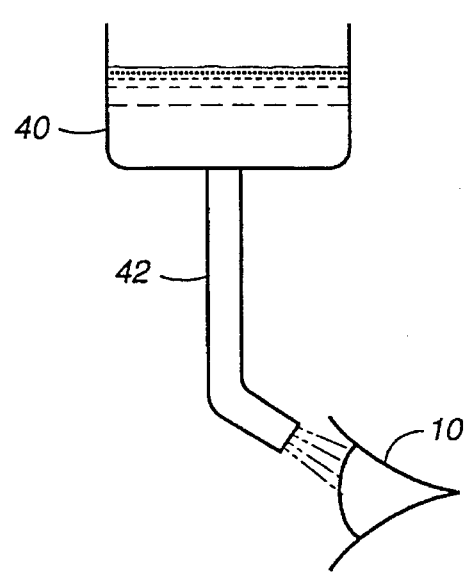
FIG._7A
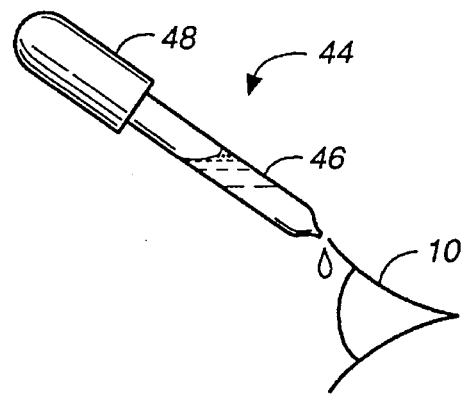
FIG._7B
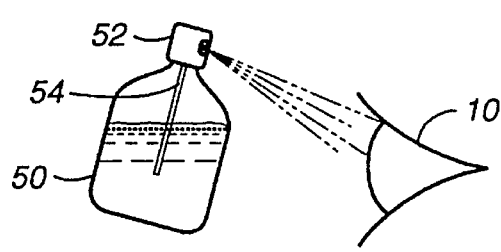
FIG._7C

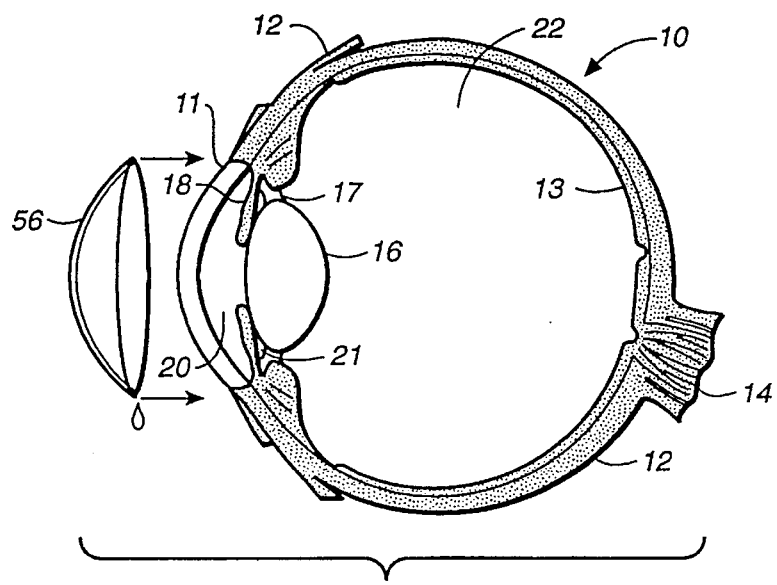
FIG._8A
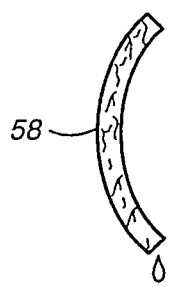
FIG._8B
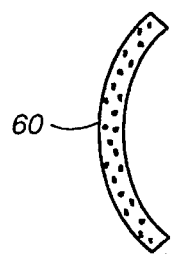
FIG._8C
FIG._8D
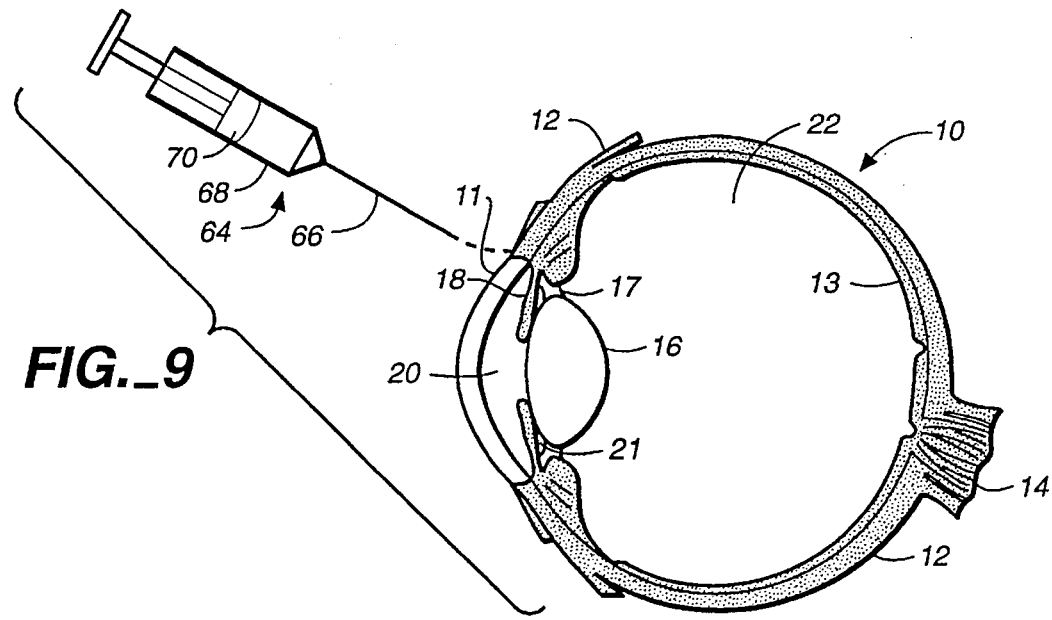
FIG._9

COLLAGEN TREATMENT APPARATUS

CROSS-REFERENCE TO RELATED APPLICATIONS

This is a continuation of application Ser. No. 08/227,781, filed Apr. 14, 1994 and now U.S. Pat. No. 5,484,432, which is a continuation-in-part of the following United States Patent Aapplications: (1) application Ser. No. 07/926,331 (filed Aug. 6, 1992 and now U.S. Pat. No. 5,374,265), which is a continuation-in-part of application Ser. No. 07/546,252 (Jun. 29, 1990 and now U.S. Pat. No. 5,137,530), which is a continuation-in-part of application Ser. No. 07/374,958 (Jun. 30, 1989 and now U.S. Pat. No. 4,976,709), which is a continuation-in-part of application Ser. No. 07/285,379 (Dec. 15, 1988), which is a continuation of application Ser. Nos. 07/170,070 (Mar. 14, 1988), abandoned, 07/067,381 Jun. 23, 1987, abandoned, and 06/914,169 (Oct. 1, 1986), abandoned, the latter being a continuation-in-part of application Ser. No. 06/781,225 (Sep. 27, 1985), abandoned; and (2) application Ser. No. 07/930,973 (Aug. 17, 1992 and now U.S. Pat. No. 5,304,169), which is a continuation-in-part of application Ser. No. 07/771,547 (Oct. 4, 1991), now abandoned, which is a continuation-in-part of application Ser. No. 07/546,252 (Jun. 29, 1990 and now U.S. Pat. No. 5,137,530), which is a continuation-in-part of application Ser. No. 07/374,958 (Jun. 30, 1989 and now U.S. Pat. No. 4,976,709), which is a continuation-in-part of application Ser. No. 07/285,379 (Dec. 15, 1988), abandoned, which is a continuation of application Ser. Nos. 07/170,070 (Mar. 14, 1988), abandoned, 07/067,381 Jun. 23, 1987, and 06/914, 169 (Oct. 1, 1986), abandoned, the latter being a continuation-in-part of application Ser. No. 06/781,225 (Sep. 27, 1985), abandoned.

All of the above-referenced United States Patents and Patent Applications are incorporated herein by this reference. Additionally, incorporated herein by these further references are the entire disclosures of application Ser. No. 08/160,405 (Dec. 2, 1993) of inventors Michael J. Berry, David R. Hennings and Arthur V. Vassiliadis, and application Ser. No. 07/923,813 (Aug. 3, 1992) of inventors David R. Hennings and Ralph W. Olenick.

BACKGROUND OF THE INVENTION

Collagen connective tissue is ubiquitous in the human body and demonstrates several unique characteristics not found in other tissues. It provides the cohesiveness and tenacity of the musculo-skeletal system, the structural integrity of the viscera, as well as the elasticity of the integument.

Most endothelial-lined structures of the body have collagen cores for specific functional purposes. Collagen cores are found in structure as diverse as the trabecular meshwork of the aqueous filtration system of the eye, and the valves of the heart. The walls of the great vessels share their collagen integrity with the ligamentous bony attachments and the tendinous or sinewy muscular attachments to the long bones. The cornea of the eye is a unique example of collagen connective tissue with the cornea stroma (accounting for about 90% of the total thickness of the cornea) demonstrating a high transparency of cross-oriented individual sheets or lamellae of collagen with a high (about 70%) water content and lesser (about 8%) amounts of protein and muco-polysaccharides.

Intermolecular cross-links provide collagen connective tissue with unique physical properties of high tensile strength and substantial elasticity. The extracellular matrix of this tissue consists of complex macromolecules, the biosynthesis of which involves several specific reactions that are often under stringent enzymatic control. The cross-linking is mediated, for example, by the copper-dependent enzyme lysyloxidase, and can be inhibited by chemicals such as B-aminoproprionitrile, as well as by various types of energy such as heat and photonic radiation. The net accumulation of collagen connective tissue is then dependent upon the precise balance between the synthesis and degradation of the connective tissue components.

A previously recognized property of hydro-thermal shrinkage of collagen fibers when elevated in temperature to the range 60° to 70° C. (an increase of about 30° C. above normal body temperature) is but one of the unique characteristics of this tissue not exhibited by other body tissues. Temperature elevation ruptures the collagen ultrastructural stabilizing cross-links, and results in immediate contraction in the fibers to about one-third of their original lineal dimension, while increasing the caliber of the individual fibers without changing the structural integrity of the connective tissue.

The present invention is directed to a method and apparatus for effecting controlled lineal contraction or shrinkage of collagen fibers to provide a multitude of nondestructive and beneficial structural changes and corrections within the body. The invention has application to the alteration of collagen connective tissue throughout the body, and will be described with specific reference to correction of refractive disorders of the cornea of the eye.

These applications have received some discussion in existing literature, but presently known techniques do not provide an adequate basis for effective use of this knowledge of the properties of collagen as a safe and predictable treatment method.

The cornea is a layered structure which provides the majority of the eye's refractive or focusing power for incoming light rays which are transmitted through the crystalline lens of the eye to light-sensitive receptors of the retina. The corneal layers, from outer to inner surfaces, include the epithelium, Bowman's membrane, a relatively thick central stroma formed of cross-oriented collagen ribbons or sheets, Descemet's membrane, and the endothelium. The as-yet unmet challenge is to achieve a thermal profile within the stroma to attain controlled, predictable collagen shrinkage and resulting corneal shape change and adjustment of refractive effects without damaging the adjacent layers.

An earlier approach to corneal reshaping to correct vision defects involved direct application of a heated probe to the corneal epithelium to transmit heat to the stromal collagen fibers. This technique, sometimes called thermokeratoplasty or TKP, was substantially unsuccessful in that peak temperatures were necessarily achieved in the outer corneal layers rather than in the stroma where the beneficial effect of collagen heating was desired. The most serious and discouraging problem was irreparable temperature damage to the corneal epithelium and its basement membrane, with consistent findings of thermal dissolution and persistent defects in this membrane. This has resulted in faulty epithelial adhesion and recurrent corneal epithelial erosions.

In contrast to corneal-stroma problems encountered in previous investigations, the desired method herein disclosed achieves highest shrinkage temperatures in the midstroma, and lowest in the region of Descemet's membrane and the endothelial monolayer on the inner surface of the cornea. The thermal profile must be controlled within a narrow peak range of 5° to 7° C. in order to destabilize the covalent bonding (or to disrupt interchain hydrogen bonds) of this triple-helical collagenous domain to achieve desired shrinkage, and without significantly traumatizing the keratocytes or denaturing the collagen fibrils. The thermal trauma associated with earlier efforts in this field leads to an acute inflammatory tissue response which results in the removal of denatured collagen, and is characterized by the deposition and subsequent cross-linking of newly elaborated collagen at the site as catalyzed by the enzyme lysyl oxidase.

The rapid replacement of contracted collagen fibers by new mature collagen following trauma results in the unwanted reversal of the desired corneal reconfiguration. In the absence of trauma, the half life of Type I collagen has been shown to be consistent with the life of the experimental animal.

Prior investigations, however, have not considered the importance of the atraumatic attainment of the proper thermal profile for protracted or permanent recurving of the cornea in the absence of collagen fibrillar replacement associated with trauma and the resulting inflammatory response.

Damage to the endothelial monolayer is the most disturbing problem encountered when the peak temperature is too far posterior in the cornea. Factors influencing the quality of this most important corneal layer include the absolute number of viable endothelial cells, and the morphology of these cells. Endothelial cells, unlike epithelial cells, are not replaced following trauma. There are several studies suggesting that cell shape (polymegathism and pleomorphism) is more closely related to the functional reserve of this layer than to endothelial cell density, but in either case complications will result in persistent edema, bullous keratopathy and loss of transparency of the cornea.

The problem of confining peak temperature to the stroma while maintaining acceptably lower temperatures in the inner and outer adjacent corneal layers is recognized in the prior art. U.S. Pat. Nos. 4,326,529 and 4,381,007, for example, disclose use of radio-frequency heating while irrigating the outer corneal surface with a cooling saline solution. Published reports on the technique, however, note ciliary spasm and fluctuating corneal power (topographic hysteresis) up to two months postoperatively. All patients had stroma scarring after the procedure, and the flattening induced was short lived.

The emergence of the laser as a practical tool for ophthalmologists has led to investigation of the use of coherent energy as a means for achieving corneal shape change to correct vision defects. One such application, essentially unrelated to the present invention, is disclosed in U.S. Pat. No. 4,461,294 which proposes the laser as a tissue-destructive (ablative photodecomposition) tool for forming radial corneal scars in a technique called radial keratotomy.

Use of the laser as a corneal collagen-shrinking tool has also been disclosed in the literature, but not in the context of a practical system which avoids tissue necrosis in the corneal epithelium, while providing predictable reconfiguration of the tissue without loss of transparency. The known technology thus does not disclose a procedure which avoids tissue necrosis, and produces protracted or permanent corneal recurving proportional to energy distribution, and repeatable (as indicated by animal studies) for similar exposure patterns and energy level.

The literature suggests that by properly selecting the absorption coefficient and using heat removal at the corneal surface, a proper temperature profile can be achieved in the cornea (high in the stroma and low in both the epithelium and endothelium). These studies conclude that the absorption coefficient must be in the range of 190 $cm^{-1}$ for this to occur; this restricts the range of wavelength interest to 2.6 or 3.9 microns; and that no lasers are commercially available at those wavelengths. This conclusion that the proper thermal profile is solely wavelength dependent is incomplete and has discouraged investigation in other wavelength domains. It is further believed that earlier investigations have incorrectly assumed that the absorption coefficient of corneal stroma is closely approximated by the absorption coefficient of water.

The present invention recognizes that in addition to absorption coefficient and anterior surface heat removal, the footprint of the energy with time significantly influences the temperature profile in the cornea. Specifically, by using pulsed or burst mode energy, a proper temperature profile has been obtained at much lower absorption coefficients (15–120 $cm^{-1}$), allowing use of lasers operating in the range of 1.80–2.55 micron wavelengths within today's technology. This method avoids the trauma of improper thermal profiles, and obtains proportional changes from at least 2 to 13 diopters in refractive power related to exposure pattern and energy density. This method has been shown to be repeatable in that similar changes in corneal curvature were observed for similar patterns and exposure levels. Significant induced effect has persisted throughout follow-up investigation, lending evidence that the half-life of corneal collagen was undisturbed.

My U.S. patent application Ser. No. 07/546,252 and U.S. Pat. No. 4,976,709, the entire disclosures of which are incorporated herein by reference, describe methods and apparatus for achieving controlled shrinkage of collagen tissue. These prior inventions have application to collagen shrinkage in many parts of the body, and are particularly useful in an ophthalmological procedure for achieving controlled shape changes in the cornea of the eye for correction of refractive errors.

As described in detail in the application and patent which are incorporated by reference (directly above), a presently preferred collagen-shrinkage technique involves use of laser coherent energy in a wavelength range of about 1.80 to about 2.55 microns, or of such coherent infrared energy of wavelengths corresponding to collagen absorption coefficients in the range of about 15 to 120 $cm^{-1}$. Irradiation of collagen with such energy is controlled to elevate the collagen temperature to at least 23° C. above normal body temperature to achieve collagen shrinkage.

As explained in my referenced prior disclosures, a critical factor in shrinkage of corneal collagen of the eye is avoidance of excessive tissue-destructive temperature increases throughout the corneal stroma, and especially in the outer epithelial and inner endothelial layers of the cornea. A lowering of the threshold temperature at which collagen shrinkage occurs will provide an added measure of safety in avoiding tissue-destructive temperature increases, and it is to this goal that the present invention is directed.

SUMMARY OF THE INVENTION

This invention is directed to collagen connective tissue shrinkage by the use of laser coherent energy in the infrared wavelength range of about 1.80 to 2.55 microns, and preferably in the range of about 2.0 to 2.2 microns, as generated by a solid-state device such as holmium-doped yttrium-lithium-fluoride (YLF) or yttrium-aluminum-garnet (YAG) crystal laser. This type of laser is relatively compact and easy to operate, and is capable of generating energy optimally absorbed within collagen tissue based on the spectral-absorption coefficients of these wavelengths, without damage or destruction of adjacent tissue.

In an ophthalmological context, the invention relates to laser keratoplasty using a laser having the aforementioned characteristics for collagen shrinkage and consequent reshaping of the cornea for correction of vision errors or defects. Irradiation and resulting heating of the corneal stroma is preceded by measurement or mapping of the untreated cornea contours, and computation of the specific corneal regions to be heated to produce the desired corrective reshaping.

Timing of energy delivery to the corneal stroma is an important factor in achieving an intracorneal temperature profile which peaks in the generally central and anterior portion of the stroma, while limiting temperature increases to safe and nontraumatic levels in the corneal tissue layers anterior and posterior of the stroma. The energy should be delivered in less than one second, and preferably in about 100 milliseconds (pulse or burst modes) to position the peak temperature correctly within the stroma. These techniques enable the use of irradiating wavelengths in the 1.80–2.55 micron range with relatively low absorption coefficients in the general range of 15 to 120 $cm^{-1}$.

This invention relates to a process for collagen shrinkage by application of coherent infrared energy, preceded by application of a reagent to the collagen tissue for reduction of the shrinkage threshold temperature. Presently preferred reagents include hyaluronidase, and (especially) lysozyme. The resulting thresh old-temperature reduction of about 10° to 12° C. enables use of lower energy levels. The infrared energy is preferably supplied by a laser operating in the wavelength range of about 1.8 to about 2.55 microns.

The invention is described with specific reference to ophthalmic applications in which a corneal shape change is effected to correct refractive errors of the eye. In this application, the reagent is mixed with an anaesthetic, and the mixture is impregnated in a contact-lens-like corneal collagen shield which is then applied to the cornea. After the mixture is absorbed by the cornea, the laser energy is applied, preferably repetitively in different corneal zones, to heat the corneal stroma, and thereby to cause the desired shrinkage and shape change.

BRIEF DESCRIPTION OF THE DRAWINGS

FIG. 1 is a horizontal sectional view of an eye;

FIG. 2 is a schematic cross-sectional view of the cornea;

FIG. 3 is a block diagram of the apparatus of the invention;

FIG. 5 is a plot of temperature elevation within the cornea;

FIGS. 7a–7c are schematic illustrations of means for the topical application of reagents or drugs to an eye, FIG. 7a illustrating a continuous irrigation device, FIG. 7b illustrating a periodic irrigation device, and FIG. 7c illustrating an aerosol device;

FIGS. 8a–8d are schematic illustrations of means for delivering reagents or drugs to an eye, FIG. 8a illustrating a soft contact lens or corneal collagen shield to be placed on the cornea of the eye, FIG. 8b illustrating in two dimensions a soaked pledget to be similarly placed on the cornea, FIG. 8c illustrating in two dimensions a soaked sponge to be placed on the cornea, and FIG. 8d illustrating in two dimensions a membrane or reservoir device to be placed in an eyelid or the conjunctival sac; and FIG. 9 is a schematic illustration of subconjunctival injection of reagents or drugs to an eye.

DETAILED DESCRIPTION OF THE PREFERRED EMBODIMENT

Figure 4:
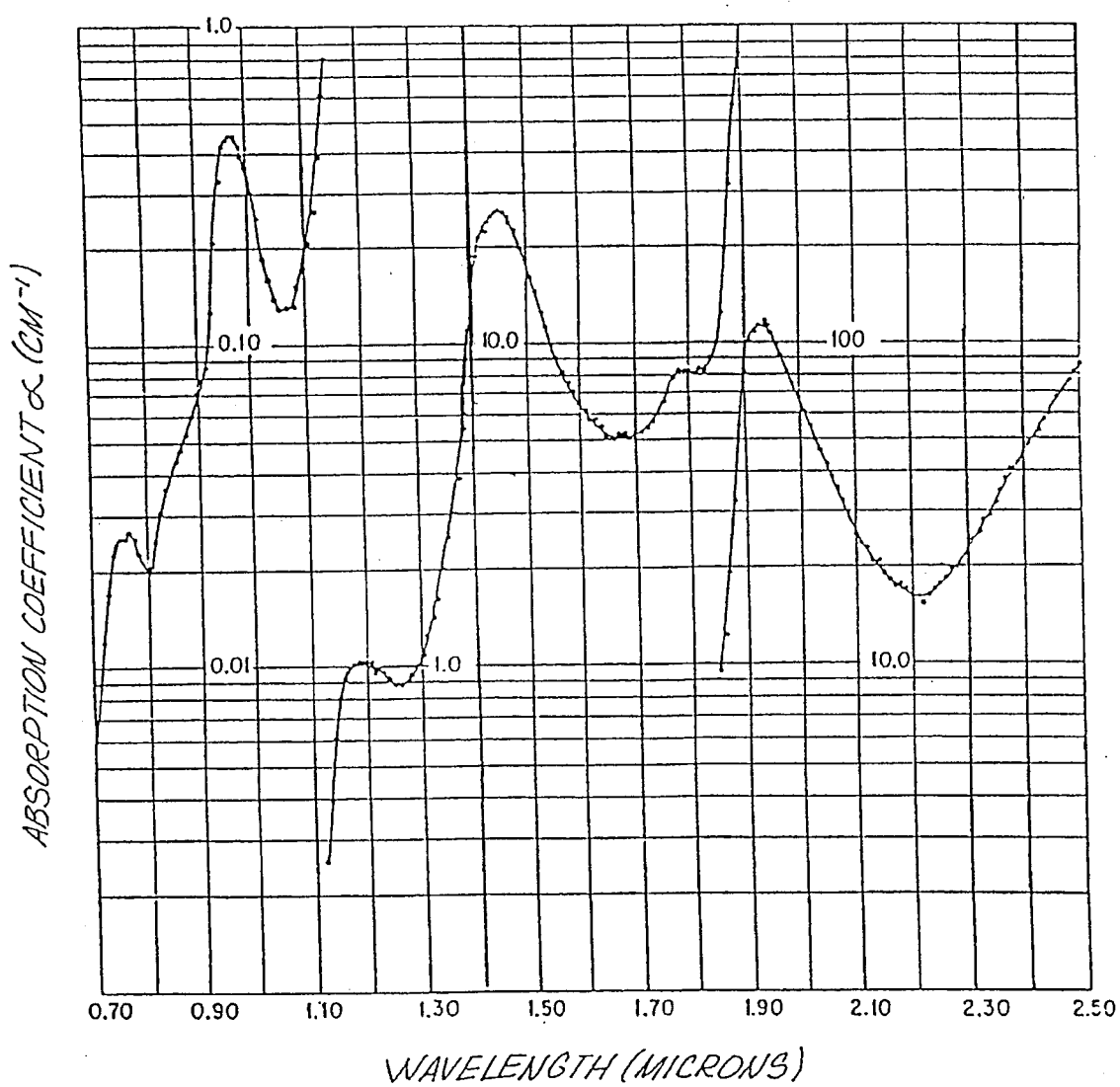
FIG. 4 is a plot of the absorption coefficient of distilled water as a function of incident wavelength.

The invention will be described in terms of a laser keratoplasty (LKP) system for shape modification of the human cornea, but the inventive principles are applicable to collage shrinkage in other parts of the body. The LKP application is in a sense the most challenging use of the invention in view of the critical need to confine the heat field to target portions of the corneal stroma while avoiding excessive and potentially damaging temperature elevations in the sensitive tissues adjacent the stroma.

As a quick review of the anatomy of the eye, FIG. 1 is a horizontal section of an eye 10 having a roughly spherical structure with a transparent cornea 11 at the forward central portion, the remainder of the sphere of the "eyeball" being white and opaque sclera 12 which is attached to and blends with the periphery of the cornea. The eye's light-sensitive retina 13 extends along the rear and part of the forward inner surface of the sclera, and is connected to an optic nerve 14 which extends to the brain.

Positioned behind the cornea is a crystalline lens 16 supported by zonular ligaments 17, and the lens is capable of shape changes which enable the eye to focus on objects at various ranges. The eye's iris 18 is positioned between the cornea and lens to divide the space forward of the lens into an anterior chamber 20 and posterior chamber 21 which are filled with a clear and watery fluid called aqueous humor. The space behind the lens is filled with a clear gel-like body 22 called vitreous humor.

FIG. 2 is an enlarged schematic representation of the corneal cross-section to show the various layers of the cornea as already briefly discussed. The outermost or anterior layer is the epithelium 25 (typically about 50 microns thick and accounting for about ten percent of total corneal thickness) and its underlying basement membrane. The next layer is Bowman's membrane 26 (about 10–13 microns thick in the human eye) which is nonregenerative. The main body (about 90 percent of the total thickness) of the cornea is stroma 27 composed of clear sheets of collagenous material. The stroma is backed by Descemet's membrane 28 (about 5–10 microns thick), and the innermost or posterior layer is endothelium 29 which is a single layer of nonreproducing flattened cells of about 4–5 microns thickness.

The geometry of the cornea is complex, but has surfaces which are approximately concentric and spherical, the radius of curvature of the outer or anterior surface typically being about 8 millimeters. This value is smaller than the average radius of curvature of the sclera, giving the cornea a bulged appearance with respect to the sclera. The corneal diameter (greatest chord) is about 11 mm, and total thickness at the corneal center is about 0.55 mm.

From the structural standpoint, the characteristics of the cornea can be determined and predicted by an analytical model embodying the following corneal qualities:

a. The cornea is a thin dome-shaped shell supported peripherally by the sclera, and internally by uniformly destributed fluid pressure of the aqueous humor in the anterior chamber.

b. Zones or portions of the corneal shell which are heated to above about 60° C. will predictably shrink as the collagen lamellae of the stroma contract to about 30% of original length.

c. It is theorized that the corneal shell is sufficiently elastic to permit the fluid-pressure-supported posterior surface to retain substantially its original contour, and to force shrinkage-induced contour changes to occur primarily at the anterior surface where the refractive correction is of greatest effect. This effect is aided by confining shrinkage-producing stromal temperature elevations to the anterior part of the collagenous stroma.

About three-fourths of the eye's refractive power is determined by corneal curvature, and shape modification of this element of the eye's optical system thus provides a powerful tool in correction of refractive errors. Increasing the radius of curvature of the cornea will correct myopia (nearsightedness), and reduction of this parameter will correct hypermetropia (farsightedness). A properly patterned application of corneal shrinkage energy is also effective in correcting astigmatic errors.

To correct visual defects by laser keratoplasty, it is first necessary to measure existing vision and corneal shape or topography using a commercially available corneal mapping system 33 (FIG. 3) for contour determination along the meridians of the eye. This information forms the basis for instructions generated by a computer 35 (based on the corneal shell characteristics discussed above) as to the zones of the cornea which should undergo shrinkage to effect a change in the refractive power of the cornea for correction of defects. The remaining task is to achieve the desired temperature elevation in a controller and safe fashion.

The laser is a useful tool in medicine for applying controlled and focused radiant energy for localized heating of tissue, and-widely used in ophthalmology (e.g., for retinal repairs), and other specializations such as gynecology and otolaryngology. Depending on the use, these instruments may emit coherent energy in the visible-light band or may operate in the infrared or ultraviolet portions of the electromagnetic spectrum. These applications, however, are nearly all directed to photocoagulation, incision, perforation, or other tissue-destructive processes.

In the present invention, the desire is to heat selected areas of collagen tissue to shrinkage levels, but without damage or destruction of either the target or surrounding tissues. Preferably, the optical-delivery-system laser is integrated with the corneal mapping or topography system to enable computer control of laser output, as well as real-time or near-real-time monitoring of progressive corneal reconfiguration.

The conversion of coherent radiant energy to temperature elevation of a target is largely dependent on a physical parameter of the target tissue body called the optical absorption coefficient, which is a variable dependent on wavelength. It has previously been proposed (see, e.g., Mainster, Martin A., "Ophthalmic Applications of Infrared Lasers—Thermal Considerations," J. Invest. Ophthalmology 1979; 18:414) that the absorption coefficient of corneal collagen in the near infrared is approximated by that of water. The wavelength dependency of this variable has been previously disclosed, and FIG. 4 is a textbook graph plotting absorption coefficient (water) against wavelength.

My research, based in part on a finding that the absorption coefficient of collagen does not accurately correspond to that of water, has established the feasibility of using lasers which emit wavelengths in the range of about 1.80 to 2.55 microns where the collagen absorption coefficient is in the range of about 15 $cm^{-1}$ to about 120 $cm^{-1}$. Wavelengths corresponding to lower absorption coefficients may produce insufficient midstromal heating. Wavelengths corresponding to significantly higher absorption coefficients tend to move the peak of the temperature profile forwardly, creating a risk of epithelial damage.

Preferably, coherent radiation with wavelengths in the range of about 2.0 to 2.2 microns is used. Coherent radiation can be generated in this wavelength by a solid-state laser 36 using holmium-doped YAG or YLF crystals as mentioned above. These lasers are mechanically and optically relatively simple and easy to operate.

These solid-sate lasers are believed to be superior to previously proposed gas lasers such as argon, krypton, HCl, and frequency-doubled CO systems. Argon and krypton lasers do not generate needed power levels. The HCl gas laser is a large laboratory instrument requiring large amounts of consumable gasses and major subsystems to create high flow rates under vacuum conditions and to chemically scrub the volatile gas reaction products. The frequency-doubled CO laser is large, and it is uncertain whether a suitable nonlinear crystal for frequency doubling at the required power level can be developed.

The research underlying this invention includes experiments with human corneal collagen tissue irradiated with pulses of about 0.10 second duration by a laser operating at about 2.1 microns at an energy level of about 0.5 joule. The predicted stromal collagen shrinkage occurred without loss of corneal transparency, and without damage to the epithelium, Bowman's membrane, or the strata underling the corneal stroma.

Protection of the corneal layers anterior to the stroma is afforded by a slightly lower surface temperature, and by the normal tear layer on the epithelium. This protection can be increased by flowing either inert gas or liquid over the cornea during irradiation. Another technique for conducting heat from the corneal surface is to apply a contact lens "window" of a material such as sapphire which has high thermal conductivity and thermal mass.

FIG. 5 shows the computed temperature profile through the corneal thickness using a 2.1 micron solid-state laser irradiating a circular corneal area having a radius of about 1.5 mm for 0.1 seconds with about 0.5 joule of energy incident on the cornea, and using flowing-irrigant cooling of the corneal surface. The significant feature is that desired peak temperatures are confined to the anterior stroma (just forward of the cross-sectional centerline of the stroma) as shown in FIG. 5, and the adjacent corneal layers are not heated sufficiently to present a risk of tissue damage.

A key objective is to achieve a shrinkage-producing temperature elevation of at least 23° C. in the stroma, while preventing destructive temperature increases in the corneal epithelium and endothelium, and preserving corneal transparency. This goal is achieved by use of the recommended coherent wavelengths (and associated absorption coefficients) at moderate energy densities in a range up to about 100 joules per square centimeter, and relatively short-duration energy pulses (burst or pulse mode, or gated c-w) with a width in the range of 0.010 to less than 1.0 seconds, and preferably about 100 milliseconds. Preferably, a higher-power shorter-duration pulse is used (rather than a low-power long-duration exposure) to achieve the necessary temperature elevation with minimum thermal losses within the eye, and delivery of lower total energy to the eye.

A very short high-energy pulse presents a risk of excessive epithelial heating because there is insufficient time for the heat-removal mechanisms mentioned above (for example, a puff of cooling gas) to act. A long-duration pulse, on the other hand, leads to excessive conductive dissipation of heat within the stroma and away from the target shrinkage volume. A presently preferred "exposure time" for delivery of energy is 100 milliseconds for each element or spot in a shrinkage pattern.

Experimental efforts conducted to date have involved application of temperature-elevating energy to specific spaced-apart stromal zones in a series of dots which are small circles in the range of about 0.25 to 2.0 mm in diameter. The patterning of these dots depends on the kind of refractive correction which is needed. For example, a pattern of dotted radial spokes extending from an untreated central circular part of the cornea is effective in correction of myopia. A dotted circular pattern centered on the corneal axis is used for correction of farsightedness. One or more dotted linear arrays on a meridian is used for astigmatic corrections. These patterns do not involve application of shrinkage energy to the visual axis of the eye.

The treatment method is not limited to application of shrinkage heating in a "stitched" pattern of circular dots. For example, if energy is applied in a series of time-separated dots, the individual dots need not be circular, and a rectangular or other dot shape may be used to achieve a desired shrinkage effect. It is also optically possible to apply the shrinkage energy as a narrow line, or as a pattern of lines forming a rectangle or other shape. Thus, for example, a single application of heating energy can be in a circular or toroidal pattern.

In planning specific treatment programs, it is useful to consider energy density in determining the pattern of shrinkage radiation. Experimental results indicate that energy densities up to about 100 joules per square centimeter are consistent with establishing a desired temperature profile within the stroma, while preventing excessive heating in the tissue layers adjoining the stroma. Depending on the selected energy pattern, the applied energy per "shot" is typically in the range of about 0.01 to 5.0 joules.

It is also within the scope of this invention to apply multiple shots of temperature-elevating energy to each stromal zone in which shrinkage is to be effected. This can in some cases provide more accurate control of the profile of temperature increase within the stroma. For example, two or three energy pulses (each of about five to ten milliseconds duration) may be applied to a single zone, with short-duration interpulse separation of about 50 to 200 milliseconds.

This invention achieves controlled intrastromal shrinkage without causing thermal trauma and collagen coagulation, and a resulting unwanted inflammatory tissue response. Avoidance of the inflammatory response (a problem characteristic of prior-art investigations) is an important factor in achieving a long-duration chronic shape change of the cornea for correction of visual defects.

Figure 6:
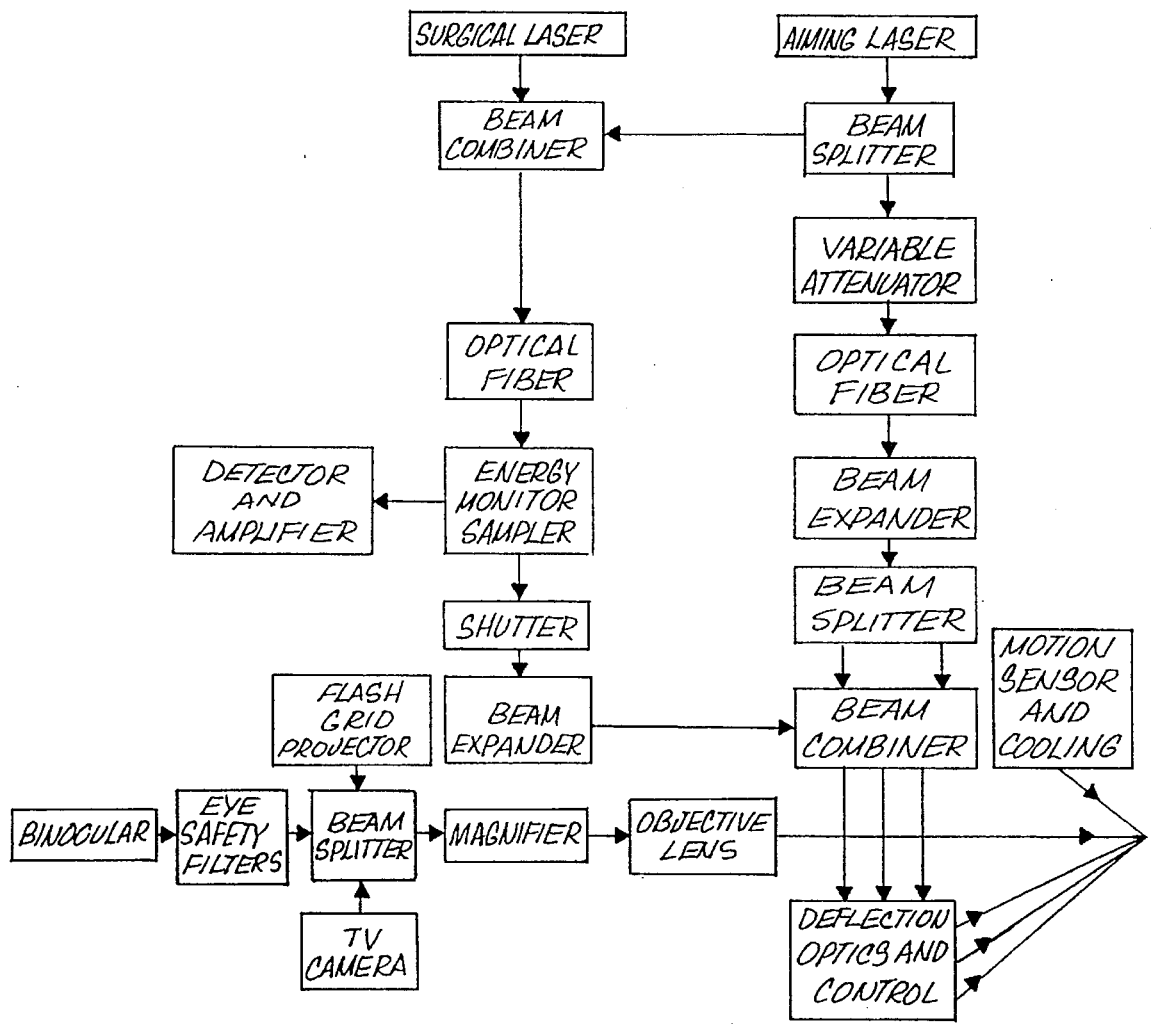
FIG. 6 is a block diagram of an optical delivery system.

The overall system may take different forms, and one arrangement is shown in FIG. 6 which illustrates in block-diagram form an optical delivery system which includes a low-power aiming laser, a means for sensing unwanted eye movement, and the various associated controls and displays. Measurement of the refractive properties of the cornea before, during and after treatment is made by a corneal topography measuring device. One suitable such device identified as a "Corneal Analysis System," is marketed by EyeSys Laboratories, Houston, Tex.

Corneal measurement systems of this type typically make available a color CRT screen display of contour data, as well as printout of the corresponding information. These systems identify the astigmatic axis and permit selection of desired meridians of the cornea, and present in digital and false-color display either refractive power in diopters or radius of curvature (typically in millimeters). Data-acquisition optics are preferably positioned on the slitlamp base of the laser optical delivery system, with a working distance of about three inches from the corneal surface.

These systems typically have adjustable measurement fields (e.g., 0.8 mm to 7 mm, with a 42.5 diopter sphere), and achieve a resolution of about plus-or-minus one-quarter diopter over the full selected field. Data-processing time is rapid (in the range of twenty seconds from measurement to printout or screen display) and nearly real time, and image-subtraction routines enable rapid calculation and display of corneal-healing refractive change by comparing pre- and post-application images. This noncontacting measuring system does not affect corneal surface integrity, and the convex-mirror quality of the cornea is undisturbed as required for the image-subtraction technique and other post-energy-application measurements.

Laser thermal keratoplasty using the laser exposure parameters discussed above provides an optimal thermal profile in the anterior and midstroma of the cornea for collagen fibrillar contraction. This profile is defined as 25° C. to 30° C. above the normal physiologic temperature, while maintaining substantially physiologic temperature in the epithelium and endothelium.

Collagen is considered to be metabolically inert in its steady state, and while thermally induced contraction occurs by the process of this invention, temperature elevations are below the thermal traumatic or inflammatory thresholds. In the absence of trauma, the dimensional collagen reconfiguration is believed to exhibit long-term stability.

The type-I collagen molecule consists of chains of 300-nm triple helixes joined by 67-nm uncoiled bonds. Controlled contractions of the individual fibrillar molecules require an exposure pattern consistent with magnitude and radial arc modifications desired.

An increase in the radius of curvature of the cornea results in the effective shortening of the focal length of the visual system of the eye, while a decrease in the radius or steepening of the cornea increases the focal length. A correction of myopia requires an increase of the radius, while hypermetropia is treated by decreasing the corneal radius of curvature. Corneal astigmatism is modified by flattening in the myopic meridian, while an opposite effect occurs at right angles to this recurvature.

This thermal keratoplasty process, therefore, requires not only an optimal thermal profile in the sagittal dimension, but to be effective in the modification of refractive error, also requires an exposure pattern in the plane of the corneal surface consistent with the desired magnitude and direction of radial arc changes. Studies on experimental animals have identified several exposure patterns resulting in corneal curvature modifications for myopic, hypermetropic, and astigmatic errors.

A 2–3 mm central laser exposure spot in the visual axis results in a maximal flattening of the corneal radius of curvature of from 0.5 to 18 diopters, depending upon energy level and exposure duration. A transient stromal haze occurs, but fades within 48 hours following energy application.

In order to avoid exposure in the visual axis, two additional effective flattening patterns have been identified. Each of these patterns or arrays spare the 3-mm central optical zone.

One array utilizes a symmetrical radial pattern of six to eight lines each comprising about six individual 0.5-mm spots spaced about 0.5-mm apart. Ten diopters of flattening has been obtained with this pattern.

Another, and perhaps most desired pattern, is the circumferential distribution of individual 0.5-mm exposures, sparing the 3-mm central optical zone. No haze is experienced and up to 15 diopters of myopic correction has been obtained with a multipulsed laser. The resulting refractive correction has persisted throughout an observation period exceeding 18 months. Since an inflammatory tissue response does not occur, it is likely that the reconfiguration is of protracted duration, and perhaps permanent.

Steepening occurs over a large range of corrections as the ring or circumferential pattern encroaches upon the peripheral cornea beyond 5 mm from the visual axis. Similar long-term duration is obtained.

Meridional modification is obtained by parallel lines 3-mm apart, and above and below the central optical zone in the direction of the meridian, each line utilizing 5 or 6 individual 0.5-mm exposure spots.

There has been described a new and effective system for irradiation of collagen tissue to produce corrective shape changes by controlled and predictable collagen shrinkage. While disclosed as a corneal shape-modifying technique, the system has application to other collagenous bodies, and is believed useful in fields ranging from cosmetic surgery to correction of defective heart valves or musculoskeletal injuries.

Interstitial collagen (Type I) consists of a continuous triple helical molecule which is 300 nanometers in length. The parent molecule is procollagen. The triple helix is formed by three polypeptide chains. Each chain forms a left-handed polyproline II helix which interacts with two other helices to form a right-handed superhelix.

Mammalian collagen is generally considered to be stabilized by electrovalencies located at polar side chains to form salt-like cross-linkages, and coordinate valencies between adjacent peptide groups (hydrogen bonds). Destabilization of collagen will result from removal of an amorphous substance (Glycosaminoglycan or GAG which includes chondroitin sulfuric acid or CSA) which cements collagen fibers together into fiber bundles. Destabilization also results from cleaving the intermolecular hydrogen bonds to cause a helix-to-coil transition.

Anything which interferes with the interaction of any interchain linkage will inevitably influence the thermal transformation temperature. Shrinkage temperature may be defined as the specific point at which disruptive tendencies exceed the cohesive forces, thus making this temperature an actual measurement of the structural stability of collagen expressed in thermal units.

Normal stabilized collagen fibers are stable up to a temperature of 58° C. to 60° C., and shrinkage occurs within a small temperature range between about 60° C. and 70° C. Major conformational changes occur in the molecule before unfolding, however. Predenaturational transition is observed by calorimetric measurements, and the molecule contains micro-unfolded states at temperatures below the melting temperature.

An increase in upper-limit thermal stability ($T_S$) of collagen fibers with age is interpreted as resulting from an increased number of hydrogen bonds in progressive cross-linkage of the collagen structure. This is related to progressive sclerosis. Normal tendon collagen has a shrinkage temperature threshold which is 2° C. to 4° C. less than the corresponding threshold for skin collagen.

Ultrastructural changes take place far below the point of thermal shrinkage, but collagen fibers kept for a protracted period at elevated temperatures considerably below their $T_S$ show beginning shrinkage as shown by topo-optical staining reactions and polarization optical analysis. This indicates a gradual and continuous change of the micellar texture of the collagen during the earliest stages of thermal shrinkage.

Transmission polarizing microscopy enables high-resolution observation of morphological changes and characteristics not seen with routine light microscopy. Tissue birefringence is detected by illuminating microscopic tissue section with incident light polarized 90 degrees to an optical analyzer located above the section creating a dark field.

These techniques of evaluating the gradual diminution of intensity and the color change in collagen birefringence caused by thermal alteration provide a succession of tissue damage markers and temperature ranges between the onset of collagen ultrastructural changes, helix-to-coil transition, and denaturation. Knowledge of the thermal damage coefficients for birefringent changes has been indispensable in the development of dosimetry models for the application of collagen shrinkage by means of the present method.

While these methods are disclosed for evaluating collagen shrinkage in general, special reference is made for their application to corneal stroma for the purpose of refractive modification. For safe and efficacious collagen shrinkage to result in a therapeutic benefit such as refractive modification of corneal curvature, shrinkage must occur well below the thermal damage threshold. As the damage threshold is exceeded, two orders of destruction occur.

The first order of damage results in collagen (protein) denaturation which, in turn, provides the stimulus for the inflammatory response resulting in removal of damaged tissue by the multipotential keratocyte. Subsequent fibrillogenesis yields new collagen fibrils of pretreatment dimensions, and undesired early regression of the desired refractive result. The second order of damage results in permanent pathology with folds in Descemet's membrane and endothelial destruction.

The present invention is an adjunctive process to laser-induced collagen thermal shrinkage for the purpose of increasing the margin of safety between the thermal shrinkage temperature and the thermal damage temperature.

The pretreatment of collagen connective tissue with a chemical or reagent which acts upon the CSA and/or the hydrogen bonding of the fibrils will reduce the thermal stability ($T_S$) and thus the thermal shrinkage temperature of the collagen. Examples of such chemicals are hyaluronidase, lysozyme and beta-naphthalene-sulfuric acid which degrade the CSA by eliminating the salt-like cross-linkages alone. This will reduce shrinkage temperature by 10°–12° C.

Urea, calcium chloride solution and periodic acid all break hydrogen bonds, and can, in concentrated form, excessively lower the threshold temperature by as much as 40° C. This of course means that hydrogen bond formation is the more important in determining fiber stability. Solutions of the reagents are believed to be useful in achieving a more modest reduction of shrinkage temperature by perhaps 10° to 15° C.

The cornea presents a physical barrier to drug penetration. Drugs appear to penetrate the cornea by diffusion and the rate of diffusion parallels the drug concentration. The corneal epithelium is the first barrier and drugs must enter this layer rapidly or be washed away. Cell membrane lipids which are present within the five cellular layers of the epithelium limit drug penetration. The epithelium contains hydrophilic constituents which also retard drug penetration.

For there to be clinical significance in the lowering of corneal collagen thermal shrinkage temperature ($T_S$) by means of reagents or drugs, the drugs must be presented to the cornea in a "bioavailable" manner. The bioavailability of a drug product is defined as the percentage of the reagent that is absorbed. In addition to bioavailability, the other important parameter to be considered is the "pharmokinetics" of the drug. This refers to the manner in which the patient's own tissues affect the therapeutic response. Many factors will alter each parameter and will result in the choice of method or means of administration of the reagent of regard.

Among the pertinent factors are the excipients or inactive compounds present in the drug such as diluents, lubricants, binders and the like which are important determinants of bioavailability. Variation in dissolution rate is also important. The pH of a drug solution determines whether it is in the ionized or non-ionized form. The non-ionized form, being more lipid soluble, is better able to penetrate the corneal epithelium. Viscosity will affect drug-corneal contact and therefore its bioavailability. Surfactants or detergents may be used to increase the solubility of drugs that are hydrophobic. Osmotics may be added to adjust the tonicity of the ophthalmic solutions to that of the tears.

Lacrimal volume will affect concentration of the drug, but reflex tearing can be minimized by the prior administration of a local anaesthetic and drug absorption can be increased by altering the corneal epithelium. Eye drop size and/or punctal occlusion will result in higher reagent concentration being available.

The reagent or drug is presented to the cornea by one of three modes of administration: (1) topical application of solutions, suspensions, ointments, powders, particulates, or the like, by periodic or continuous irrigation (FIGS. 7a and 7b), aerosol spraying (FIG. 7c), iontophoresis, or the like; (2) application of drug reservoirs such as pledgets (usually, squares of pressed cotton) or sponges soaked with a drug (FIGS. 8b and 8c), soft contact lenses soaked in a reagent (FIG. 8a), polymer drug delivery systems, collagen shields soaked in a drug (FIG. 8a), liposomes, flexible capsules or wafers, or other membrane or reservoir systems (FIG. 8d); and (3) subconjunctival injection (FIG. 9).

Of the various methods of topical administration, solutions, suspensions and ointments are the more commonly used. Suspensions should be shaken well before application to ensure that particulates are well dispersed in the suspension solution.

The combination of powders and periodic irrigation, such as by eye dropper 44 in FIG. 7b, or continuous irrigation, such as by a reagent reservoir 40 and irrigation tube 42 in FIG. 7a, may be used to lower $T_S$. As shown in FIG. 7b, periodic irrigation may be achieved by use of eye dropper 44, having reagent reservoir 46 and pressure bulb 48, to deliver reagent to eye 10. Alternatively, such periodic irrigation can be achieved by similar periodic drip systems, either manual or automated. As shown in FIG. 7a, continuous irrigation may be achieved by use of reagent reservoir 40 which feeds reagent, either by gravity or controlled feeding, to irrigation tube 42 and thereby, to eye 10. Alternatively, such continuous irrigation can be achieved by similar continuous reagent supply systems, either manual or automated.

Similarly, aerosols may be employed, such as by use of a reagent reservoir 50 and aerosol device 52, including reagent access tube 54, of FIG. 7c. Periodic or continuous irrigation, or aerosol spraying, should be used to irrigate, or to spray, the eye, respectively, with reagent for about five minutes or until the reagent has sufficiently penetrated the corneal. When periodic irrigation systems, continuous irrigation systems, or aerosol devices are used, the reagent should be applied before the blink reflex. Alternatively, means can be employed to inhibit the blink reflex and thus, facilitate the delivery of reagent by any of these systems.

Iontophoresis is largely of historical significance to aid the penetration of ionizable drugs having limited lipid solubility. This technique works by placing one electrode upon the cornea usually imbedded within a scleral contact lens in the presence of a drug solution. The other electrode can be placed anywhere else on the body. In iontophoresis, some epithelial damage may be caused by the electrode, the current, the topical anaesthetic, the hypertonic solution, and the non-physiologic pH-aided drug penetration. If the epithelium is breached, the current alters the steady state of the stroma and therefore the $T_S$, thus adding another variable that may perturbate the results.

In administration by subconjunctival injection, a syringe 64 of FIG. 9 is used to penetrate the subconjunctiva, the "mucous membrane" of the eye which lines the inner surface of the eyelids and is reflected over the fore part of the sclera and the cornea, and to deliver a reagent to the subconjunctival tissue. Syringe 64 includes needle 66, typically a 25 gauge needle, reagent reservoir 68, and plunger 70 (shown in part) of FIG. 9. In use, needle 66 is placed adjacent the subconjunctiva, as schematically illustrates by the dashed line of FIG. 9, pressured against the subconjunctiva to penetrate into the subconjunctival tissue, and plunger 70 is depressed to deliver reagent from reagent reservoir 68 to the subconjunctival tissue. Injection is usually directed to the perilimbal portion of the subconjunctiva. Certain aspects of subconjunctival injection of reagent such as patient apprehension, subsequent inflammatory response, pain, inconvenience and expense should be evaluated against the advantageous aspects of this method.

All of the drug reservoir systems and devices are effective in presenting adequate reagent to the stroma in the $T_S$ lowering process, some more efficiently than others. Pledgets 58 of FIG. 8b or sponges 60 of FIG. 8C, usually smaller than a contact lens 56 of FIG. 8a, are soaked (as indicated by a droplet) with a reagent and then placed inside one or both lids, adjacent the cornea 11 of FIG. 8a, for about five minutes or until the reagent sufficiently penetrates cornea 11. Pledget 58 may be composed of a fibrous material, such as cotton or cellulose, as illustrated by the curved and overlapping lines in the interior of pledget 58 of FIG. 8b. Sponge 60 may be composed of known sponge materials, such as cellulose, its sponge-like characteristics being illustrated by the void and non-void spaces in the interior of sponge 60 of FIG. 8c. While pledget 58 is often a cotton square, when placed adjacent cornea 11 in the same manner described below with respect to the contact lens 56 of FIG. 8a, it substantially conforms to the shape of cornea 11. Similarly, sponge 60 substantially conforms to the shape of cornea 11 when it is placed adjacent cornea 11 in the same manner. For simplicity, pledget 58 and sponge 60 are shown in two dimensions, it being understood that pledget 58 and sponge 60 have substantially the three-dimensional configuration of contact lens 56 of FIG. 8a.

While the above-described delivery systems are quite effective, drugs contained within a membrane device 62 of FIG. 8d and placed within the conjunctival sac produce a more even release of drug than any topical system. Membrane device 62 is left in the conjunctival sac for about five minutes or until the drug or reagent sufficient penetrates cornea 11. These membrane devices 62 may take the form of flexible capsules, shaped as semi-circular wafers, which are placed in one or both eyelids (usually the lower eyelid), although other forms are contemplated. While the lipophilic or hydrophilic nature of the membrane, the pore size, and the membrane thickness may mitigate the rate of drug release, such membrane systems have advantages over other modalities. For example, excipients can be avoided, tear pH is not acutely lowered and lacrimal washout is not a factor.

Liposomes, which are synthetic phospholipid vesicles, absorb to the corneal epithelium cell membrane and transfer drug directly. Liposomes are generally described in a published international patent application under the Patent Cooperation Treaty, International Publication No. WO 86/03938, of inventors John H. Crowe and Lois M. Crowe (International Filing Date of Jan. 8, 1986), on pages 1 and 2. The entire disclosure of these two pages is incorporated herein by this reference. The primary limitations of liposomes are their limited binding power to the epithelium and their expense.

Hydrophilic soft contact lenses 56 of FIG. 8a have been used as drug reservoirs with success. Polymer drug delivery systems, while effective, are generally more rigid than the soft contact lenses 56. Particularly preferred are cross-linked collagen shields, also shown as 56 of FIG. 8a, which are shaped like contact lenses 56 and are used to both promote corneal epithelial healing and to provide drug delivery. Because they conform to the shape of cornea 11, multiple base curves are not required. They also are biodegradable and thus provide protection to cornea 11 during the post-laser recovery period after the drug reservoir is dissipated and do not require removal.

As schematically shown in FIG. 8a, a pre-soaked (as indicated by a droplet) contact lens 56 or collagen shield 56 which is shaped to conform substantially to the shape of cornea 11 is placed (as indicated by the pair of parallel direction arrows) in contact with cornea 11 of an eye 10 of a patient. As further explained herein, the patient's eyelids are closed over the shield for about five minutes or until the reagent sufficiently penetrates cornea 11.

The ideal system combines administration of topical anaesthetic, such as proparacaine, with the efficient administration of reagent by means of a collagen shield. Topical anaesthetic is used to breach the epithelial barrier and to provide, simultaneously, desensitization for the laser exposure. Presenting topical anaesthesia by this method provides protracted desensitization for comfort following the laser exposure and, by way of the collagen shield, protects the surface epithelium and prevents denudation. The reagent further provides the intermolecular destabilization necessary for lowering the thermal shrinkage temperature of the collagen matrix. Since collagen shrinkage is thus effective with much lower coherent energy and thus at lower temperatures, the corneal heat sink required to protect the surface epithelium at higher temperatures is not be needed.

These and other possible ophthalmic drug administration devices and methods (including mucoadhesive polymers, particulates, liposomes, ocular iontophoresis, ocular films, ocular inserts and corneal collagen shields), are described in A. K. Mitra, *Ophthalmic Drug Delivery Systems*, 58 Drugs and the Pharmaceutical Sciences Series (February 1993). Fundamentals and applications of controlled drug delivery systems are further provided in J. R. Robinson and V. H. L. Lee, *Controlled Drug Delivery*, 29 Drugs and the Pharmaceutical Sciences Series (2nd Edition).

An effective way of titrating the reduction of thermal shrinkage temperature during laser thermal keratoplasty involves use of a corneal collagen shield which is an ophthalmological product available from companies such as Chiron and Bausch & Lomb. Soaking a shield of this type in a mixture of topical anaesthetic such as tetracaine and the desired $T_S$ reducing reagent of the appropriate concentration has several distinct advantages. The anaesthetic mixture assists in the penetration of the threshold-reducing reagent through the corneal epithelium which is a mechanical barrier for the chemical. At the same time, the cornea is anaesthetized in preparation for the laser thermal keratoplasty procedure.

The use of lysozyme to reduce the cement substance of the corneal collagenous stroma has several distinct advantages over similar reacting reagents. Lysozyme is a naturally occurring protein in lacrimal secretion, and is well tolerated by the ocular epithelial surfaces. Lysozyme is a relatively small molecule (molecular weight of about 14000, as compared to hyaluronidase of about five times greater weight) which more readily penetrates the epithelium in an anaesthetic vehicle. A more efficacious equilibrium of concentration is thereby maintained within the CSA of the corneal stroma.

The collagen shield resembles a translucent contact lens, and is fabricated from bovine or porcine collagen tissue which resembles the collagen molecule of the human eye, but it is not cross-linked. The shield promotes epithelial healing, and protects the cornea after coherent energy exposure. It lubricates and provides a heat sink during the exposure procedure, and biodegrades within approximately 12 hours.

The sustained release of the $T_S$ reducing chemical (such as urea or lysozyme) acts to gradually sensitize the stromal collagen to a reduced thermal shrinkage temperature, providing the desired thermal margin of safety, and assuring collagen shrinkage and refractive modification without the attendant damage risk of other methods.

In use, the collagen shield is placed in a shallow plastic cup (supplied by the shield manufacturer), and is irrigated with and completely immersed in about five millimeters of an ophthalmic topical anaesthetic such as tetracaine or proparacaine. About five droplets of the desired threshold-temperature reducing reagent (e.g., lysozyme) are added to the cup to provide a concentration of about 10 percent in the anaesthetic vehicle. The shield remains immersed in the anaesthetic and reagent mixture for about five minutes to assure complete absorption by the shield.

The liquid-loaded and lubricated collagen shield is then inserted against the eye surface in the same fashion used to install a soft contact lens. The patient's eyelids are closed over the shield for about five minutes to enable corneal absorption of the anaesthetic and reagent. The patient is forewarned of a probable transient discomfort as the anaesthetic is released into the lacrimal layer of the eye. After the corneal-absorption period has elapsed, the patient is positioned against the usual chin and forehead rests of a biomicroscope, and the shrinkage-producing laser exposure treatment proceeds.

The collagen shield provides a number of advantages in the overall treatment program. It provides a "sustained release" vehicle for the reagent, and maintains proper concentration within the lacrimal layer. The same sustained-release action maintains protracted anaesthesia (for several hours beyond that resulting from conventional topical application) for patient comfort after laser exposure.

The shield also lubricates the cornea during prolonged laser exposure (the blink reflex being inhibited by the anaesthetic), and promotes epithelial regeneration if cell damage occurs from prolonged anaesthetic exposure. Importantly, the shield further provides a heat sink at the corneal surface to minimize epithelial temperature elevation during laser exposure, and to maintain a desired peak-temperature profile in the anterior midstroma of the cornea as discussed in the disclosures incorporated herein by reference. The shield biodegrades after about twelve hours, and acts in much the same manner as a bandage lens during that period.

While laser exposure parameters (energy levels and duration) are adjusted to allow for energy absorption by the corneal shield, the overall result is that lower energy levels are delivered to the corneal stroma to cause the desired shrinkage. Using the reagents already described, threshold temperature is reduced to about 48° C. which is only 11° C. above body temperature, and well below the temperature at which collagen denaturation or endothelial damage is likely.

Though not fully evaluated, it is expected that laser exposure parameters (using a THC:YAG laser at 2.08 microns) will involve pulsed energy application at one to three pulses per second, with a pulse width of one to eight milliseconds, and at an energy level of about 25 millijoules.

The post-treatment of mammalian collagen, that is the use of an agent after laser exposure, will also result in enhancement of the shrinkage effect and thus increase refractive alteration. Beta-aminoproprionitrile is such an agent and will inhibit cross-linking mediated by the copper-dependent enzyme lysyl-oxidase by preventing disulphide bonds from developing.

The judicious and appropriate use of the herein disclosed methods in association with laser thermal keratoplasty as described in my referenced disclosures will yield predictable and efficacious refractive changes without undesirable damage to adjacent corneal tissue, and without the subsequent regression of refractive alteration and permanent corneal pathology.

While the invention has been described primarily in terms of corneal refractive modification, the disclosed procedure, modified appropriately for the characteristics of the target collagen tissue, will be efficacious for collagen modification throughout the body.

What is claimed is:

1. A method of modifying human tissue, comprising:
   generating radiation of a wavelength corresponding to an absorption coefficient in a range of from about 15 cm$^{-1}$ to about 120 cm$^{-1}$; and
   directing the radiation at tissue selected to absorb the radiation for a time and with an intensity to cause the selected tissue to shrink.

2. The method of claim 1, wherein the radiation wavelength is in a range of from about 1.80 microns to about 2.55 microns.

3. The method of claim 1, wherein said generating radiation includes using a laser to generate the radiation.

4. The method of claim 1, further comprising applying a reagent to the selected tissue to reduce the threshold shrinkage temperature thereof, prior to said directing of the radiation.

5. The method of claim 1, further comprising lowering a temperature of a surface of the selected tissue during said directing of the radiation.

6. The method of claim 5, wherein said lowering of the temperature of the surface of the selected tissue includes applying a heat sink to the surface.

7. The method of claim 1, wherein said directing of the radiation includes directing pulses of radiation at the selected tissue, consecutive pulses being separated by a period in which the selected tissue is not exposed to radiation.

8. The method of claim 1, wherein said directing of the radiation is thermally atraumatic to the selected tissue.

9. The method of claim 1, wherein said directing of the radiation avoids ablation of the selected tissue.

10. The method of claim 1, wherein said directing of the radiation includes directing the radiation at the selected tissue in a pattern of dots, lines, or a combination thereof.

11. The method of any one of claims 1 through 10, wherein the selected tissue is non-corneal tissue selected from the group consisting of connective tissue, musculoskeletal tissue, visceral tissue, integumentary tissue, tissue of an ocular trabecular meshwork and tissue of a coronary valve.

12. The method of any one of claims 1 through 10, wherein the selected tissue is within a stromal region of a cornea.

13. The method of claim 12, wherein said directing of the radiation avoids damage to an endothelium of the cornea.

14. A method of modifying human tissue, comprising:
   generating radiation of a wavelength in a range of from about 1.80 microns to about 2.55 microns; and
   directing the radiation at tissue selected to absorb the radiation for a time and with an intensity to cause the selected tissue to shrink.

15. The method of claim 14, wherein said directing of the radiation includes directing pulses of radiation at the selected tissue, consecutive pulses being separated by a period in which the selected tissue is not exposed to radiation.

16. The method of claim 14, wherein said directing of the radiation avoids ablation of the selected tissue.

17. The method of claim 14, wherein said directing of the radiation includes directing the radiation at the selected tissue in a pattern of dots, lines, or a combination thereof.

18. The method of claim 14, wherein the selected tissue is within a stromal region of a cornea and said directing of the radiation avoids damage to an endothelium of the cornea.

19. An apparatus for modifying human tissue, comprising:
   a source of radiation of a wavelength in a range of from about 1.80 microns to about 2.55 microns; and
   a system for delivering the radiation from the radiation source to selected radiation-absorbing tissue for a time and with an intensity to cause the selected tissue to shrink.

20. The apparatus of claim 19, wherein the radiation delivery system is characterized by delivering the radiation in a predetermined pattern of multiple locations on a surface of the selected tissue.

21. The apparatus of claim 20, wherein the predetermined pattern is a pattern of dots, lines, or a combination thereof.

22. The apparatus of claim 20, further comprising an aiming laser which is characterized by directing visible radiation therefrom toward the selected tissue according to the predetermined pattern, such that the multiple locations on the surface of the selected tissue are visible.

23. The apparatus of claim 19, wherein the radiation source includes a laser.

* * * * *

UNITED STATES PATENT AND TRADEMARK OFFICE
CERTIFICATE OF CORRECTION

PATENT NO. : 5,618,284
DATED : April 8, 1997
INVENTOR(S) : Bruce J. Sand

It is certified that error appears in the above-indentified patent and that said Letters Patent is hereby corrected as shown below:

On the Title Page, Section [73] replace:
    "[73]    Assignee: Sunrise Technologies, Fremont, Calif."
with
    --[73]    Assignee: Laser Biotech, Inc., Fremont, Calif.--

Signed and Sealed this

Twenty-third Day of December, 1997

Attest:

BRUCE LEHMAN

Attesting Officer

Commissioner of Patents and Trademarks